United States Patent [19]

Rinehart, Jr. et al.

[11] Patent Number: 4,631,149
[45] Date of Patent: Dec. 23, 1986

[54] ANTIVIRAL EUDISTOMINS FROM A MARINE TUNICATE

[75] Inventors: Kenneth L. Rinehart, Jr., Champaign County, Ill.; Gary C. Harbour, Texas Township, Kalamazoo County, Mich.; Jun'ichi Kobayashi, Tokyo, Japan

[73] Assignee: University of Illinois, Urbana, Ill.

[21] Appl. No.: 578,443

[22] Filed: Feb. 9, 1984

Related U.S. Application Data

[63] Continuation-in-part of Ser. No. 517,117, Jul. 25, 1983, abandoned.

[51] Int. Cl.$^4$ .................... C07D 515/14; A61K 31/39
[52] U.S. Cl. ..................................... 540/546; 546/85; 546/86; 540/579
[58] Field of Search ..................................... 260/244.4

[56] References Cited

PUBLICATIONS

Van Name, W. G., Trans. Conn. Acad. Arts. Sci., 11 (1902) pp. 325, 344, and Plates XLVIII and LIX.
Van Name, W. G., Bull. Amer. Museum Nat. Hist., 84 (1945) pp. 1, 22, 120 and Plate 16.
Berrill, N. J., J. Morph., 81 (1947) pp. 269–281.

Primary Examiner—Donald G. Daus
Assistant Examiner—William A. Teoli, Jr.
Attorney, Agent, or Firm—Kenneth A. Weber

[57] ABSTRACT

The subject invention concerns novel and useful antiviral compounds referred to as eudistomins. These compounds are obtainable from well-known and available marine organisms. Their utility is as antiviral agents as well as antibacterial and antitumor agents in some cases.

1 Claim, No Drawings

ANTIVIRAL EUDISTOMINS FROM A MARINE TUNICATE

CROSS REFERENCE TO RELATED APPLICATION

This application is a continuation-in-part of copending application Ser. No. 517,117, filed July 25, 1983 now abandoned.

BRIEF SUMMARY OF THE INVENTION

Novel antibiotic compounds named eudistomins were extracted from a known and available marine tunicate identified as *Eudistoma olivaceum*. Eudistomins are active against DNA and RNA viruses such as herpes simplex virus types I and II and equine rhino virus. Thus, they can be used to treat infections caused by viruses in humans, animals and plants. Some of the eudistomins also have antifungal and antibacterial activity.

DETAILED DESCRIPTION OF THE INVENTION

Description of the Organism

The organism from which the eudistomins were extracted is a marine colonial tunicate identified as *Eudistoma olivaceum* by Dr. Francoise Lafrgue, Universite de Paris VI, Laboratoire Arago, Banyuls-sur-Mer, France. Detailed descriptions of these readily-available organisms can be found in the following published references:
(1) W. G. VanName, "The Ascidians of the Bermuda Islands" Trans. Conn. Acad. Arts. Sci., Vol. 11, pp. 325–412, (1902). See p. 344 and plates XLVIII and LIX for a description of *Distoma olivaceum* which was later changed to *Eudistoma olivaceum*.
(2) W. G. VanName, "The North and South American Ascidians" Bull. Amer. Museum Nat. Hist., Vol. 84, pp. 1–476 (1945). See pages 22 and 120 and plate 16 for a description of *E. olivaceum*.
(3) N. J. Berrill, "The Structure, Development and Budding of the Ascidian, Eudistoma" J. Morph., Vol. 81, pp. 269–281 (1947).

Location of the Organisms

*Eudistoma olivaceum* can be found in many locations of the Caribbean. The animals are usually attached to mangrove roots in 1 to 6 feet of warm, stagnant water and can be easily collected by wading or snorkeling during intertidal periods. Collections of *E. olivaceum* from which eudistomins were obtained were made at the following locations:
(1) Sample IRCE 1-VII-81-3-1 was collecfted among mangroves at the northeast corner of North Cay, Lighthouse Reef, Belize.
(2) Sample 21-V-82-1-3 was collected at Spoil Island #179 in the Indian River, which is near the Smithsonian Tropical Research Center, Harbor Branch Foundation, Fort Pierce, Fla., 27°, 26.8′ N by 80°, 19.6′ W.
(3) Sample AHCE #553, Station #16-III-78-2-4 was collected at Banco Chinchorro, Mexico, 18°, 35.2′ N, 87°, 20.6′ W. It was a snorkel collection on the west side of Cayo Centro (Mangrove Island) around mangroves at 1-3 depths.
(4) Sample IRCE 2-VII-81-3-1 was collected on a small island north of Turneffe Island, Belize, in the mangroves. The best spot was a lagoon on the north, lee side.

Isolation and Purification of Eudistomins

A variety of methods can be used to isolate and purify the eudistomins from samples of the tunicate organism, for example, solvent extraction, partition chromatography, silica gel chromatography, liquid-liquid distribution in a Craig apparatus, absorption on resins, and crystallization from solvents. The isolation and purification procedure can be monitored at each step by performing thin layer chromatography (TLC) and in vitro antimicrobial assays on extracts and column fractions. Equipment, materials and methods used for isolation and characterization of these compounds are described in detail in subsequent sections entitled "Physical Characterization of Eudistomins" and "Biological Characterization of Eudistomins". The following examples are illustrative of the subject invention, but are not to be construed as limiting.

EXAMPLE 1

Extraction and Solvent Partitioning (See Scheme 1)

One and one-half kilograms, wet weight, of frozen *Eudistoma olivaceum* (Sample IRCE 1-VII-81-3-1) was extracted several times with a methanol:toluene (3:1) mixture in a blender. The combined extracts were clarified by filtration and partitioned into an upper toluene layer and a lower "polar" layer by adding 1N aqueous $NaNO_3$ solution. The layers were separated, the polar layer was extracted several times with fresh toluene, and all toluene extracts were combined and evaporated to 7.5 g of a brown oil. The polar layer was then reextracted several times with chloroform and these extracts were also combined and evaporated to 1.32 g of a brown oil.

EXAMPLE 2

Chromatography of the Toluene Extracts—Isolation of Eudistomins G, H and I

The oily residue from the combined toluene extracts disclosed in Example 1, was added to an open silica gel column and eluted with pure chloroform to give 235 mg of bioactive material. Crystallization from hexane:ethyl acetate (2:1) and recrystallization from dichloromethane gave 23 mg of colorless needles designated eudistomin G.

The hexane:ethyl acetate (2:1) mother liquor from which eudistomin G was crystallized was subjected to $C_{18}$ reversed-phase medium pressure liquid chromatography (MPLC) using a step gradient of methanol:water (1:1)→methanol as eluant. The methanol:water (9:1) cut yielded two bioactive components designated eudistomin H (16 mg) and eudistomin I (15 mg).

EXAMPLE 3

Chromatography of the Chloroform Extracts—Isolation of Eudistomins C, E, P, A, B, Q, D, J and M The oily residue from the combined chloroform extracts, disclosed in Example 1, was applied to a $C_{18}$ reversed-phase MPLC column and eluted with a step gradient of methanol:water (1:1)→methanol. A methanol:water (7:3) cut yielded 230 mg of a mixture of bioactive components. The mixture was rechromatographed on a silica gel MPLC column eluting with a step gradient of chloroform→methanol:chloroform (1:1). Bioactivity was found in the chloroform:methanol (9:1) and (95:5) column cuts.

Material in the chloroform:methanol (9:1) cut was applied to a silica gel high performance liquid chromatography (HPLC) column and eluted with a step gradient of 2%→5% methanol in chloroform. A 3.5% cut yielded eudistomin C (17 mg) and the 5% cut gave eudistomin E (18 mg).

Bioactive material from the chloroform:methanol (95:5) cut of the silica gel MPLC column (see above) was applied to a silica gel HPLC column and eluted with a step gradient of 1%→5% methanol in chloroform. The 1% cut gave eudistomin P (3.7 mg), while the 2% cut gave eudistomins A (16 mg) and B. The 3.5% cut gave eudistomin Q (0.5 mg), while the 5% cut gave eudistomin D (3 mg).

A portion of the bioactive material from the chloroform:methanol (95:5) cut of the silica gel MPLC column was acetylated and applied to a silica gel HPLC column. Elution of the column with chloroform gave the acetyl derivatives of eudistomins J (0.4 mg) and M (0.7 mg).

EXAMPLE 4

Isolation of Eudistomins K, L, N and O

Another sample (1.1 kg) of *Eudistoma olivaceum* designated 21-V-82-1-3 was extracted, partitioned and chromatographed by the methods described in Examples 1 and 3. The 2% methanol-in-chloroform cut of the silica gel HPLC column gave eudistomins K (6.2 mg) and L (4.5 mg) and a single peak containing a mixture (2.0) of eudistomins N and O.

EXAMPLE 5

Isolation of Eudistomin F

In attempting to reisolate eudistomin C from *E. olivaceum* sample AHCE #553, AHCE 16-III-78-2-4, a new compound was isolated which had identical retention times on silica gel HPLC but was resolved on coinjection with eudistomin C. This compound was designated eudistomin F.

EXAMPLE 6

Salts of Eudistomins

Since the eudistomins are weakly basic, they form salts with mineral acids such as HCl, $H_2SO_4$, $H_3PO_4$, and the like. Such salts can be prepared by suspending the eudistomins in water, adding a dilute acid until the pH of the solution is about 3 to 4, and freeze-drying the solution to provide a dried residue of the eudistomin salt. Salts of the eudistomins can be used for the same biological purposes as the parent compounds.

EXAMPLE 7

Derivatives of Eudistomins

Some of the eudistomins have free amino and hydroxyl groups available for derivatization. Thus, acyl amides and esters of the eudistomins can be prepared by methods well known to those skilled in the art. Acyl derivatives of the eudistomins can be used for the same biological purposes as the parent compounds.

Acids which can be used in the acylation of a eudistomin include (a) saturated or unsaturated, straight or branched chain aliphatic carboxylic acids, for example acetic, propionic, butyric, isobutyric, tert-butylacetic, valeric, isovaleric, caproic, caprylic, decanoic, dodecanoic, lauric, tridecanoic, myristic, pentadecanoic, palmiitic, margaric, stearic, acrylic, crotonic, undecylenic, oleic, hexynoic, heptynoic, octynoic acids, and the like; (b) saturated or unsaturated, alicyclic carboxylic acids, for example, cyclobutane-carboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentane-propionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic-aliphatic carboxylic acids, for example, phenylacetic acid, phenylpropionic acid, phenylvaleric acid, cinnamic acid, phenylpropiolic acid and naphthylacetic acid, and the like. Suitable halo-, nitro-, hydroxy-, keto-, amino-, cyano-, thiocyano-, and lower alkoxyhydrocarbon carboxylic acids include hydrocarboncarboxylic acids as given above which are substituted by one or more of halogen, nitro, hydroxy, keto, amino, cyano, or thiocyano, or lower-alkoxy, advantageously loweralkoxy of not more than six carbon atoms, for example, methoxy, ethoxy, propoxy, butoxy, amyloxy, hexyloxy, and isomeric forms thereof. Examples of such substituted hydrocarbon carboxylic acids are: mono-, di-, and trichloroacetic acid;
α- and β-chloropropionic acid;
α- and γ-bromobutyric acid;
α- and β-iodovaleric acid;
mevalonic acid;
2- and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
salicylic acid;
p-hydroxybenzoic acid;
β-resorcylic acid;
gallic acid;
veratric acid;
trimethoxybenzoic acid;
trimethoxycinnamic acid;
4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;

thiocyanoacetic acid;
cyanopropionic acid;
lactic acid;
ethoxyformic acid (ethyl hydrogen carbonate);
malic acid;
citric acid;
isocitric acid;
6-methylsalicylic acid;
mandelic acid;
levulinic acid;
pyruvic acid;
glycine;
alanine;
valine;
isoleucine;
leucine;
phenylalanine;
proline;
serine;
threonine;
tyrosine;
hydroxyproline;
ornithine;
lysine;
arginine;
histidine;
hydroxylysine;
phenylglycine;
p-aminobenzoic acid;
m-aminobenzoic acid;
anthranilic acid;
aspartic acid;
glutamic acid;
aminoadipic acid;
glutamine;
asparagine;
and the like.

Physical Characterization of Eudistomins—Materials and Methods

Open column chromatography was carried out in glass columns with 63- to 200-$\mu$ silica gel. Medium pressure liquid chromatography (MPLC) was carried out with a Milton Roy Pump, Altex Glass Chromatography Columns, and an Altex UV/VIS Detector (at 254 or 280 nm, with a 2-$\mu$L preparative flow cell). Columns were packed with J. T. Baker 20–63-$\mu$ (230–400 mesh) silica gel, or Waters Associates C$_{18}$ Prep Pak Cartridge packing material. High performance liquid chromatography (HPLC) was performed with Waters Associates 6000 A and Altex HPLC pumps, Waters Associates Variable Wavelength and Altex UV/VIS detectors, Waters Associates UK-6 and Rheodyne syringe-loading sample injectors. Altex Ultrasil Si (10 mm×25 cm) and Ultrasil ODS (10 mm×25 cm) columns were utilized. Analytical thin-layer chromatography (TLC) was performed on Brinkmann Polygram SIL G/UV$_{254}$ (0.25 mm) analytical TLC plates. The plates were developed with a solvent of 15% methanol-in-chloroform and visualized with iodine, a 1% solution of vanillin in a 1:1 mixture of sulfuric acid and water, ninhydrin spray, Sakaguchi spray, and 2,4-dinitrophenylhydrazine spray reagents. Ultraviolet (UV) spectra were obtained on a Perkin-Elmer Lambda 3 spectrophotometer, in methanol. Infrared (IR) spectra were obtained on a Beckman IR-12 double beam spectrophotometer in chloroform vs. a chloroform reference.

Proton nuclear magnetic resonance ($^1$H NMR) spectra were determined on Nicolet NT-360 and Varian XL-200 and HR-220 spectrometers. Chemical shifts are reported in ppm from tetramethylsilane. Low resolution electron ionization (EI) mass spectra were obtained on a Varian MAT mass spectrometer, Model CH-5DF. Gas chromatography (GC)/HREI and GC/CI (chemical ionization, CH$_4$ reagent gas) mass spectra were obtained on a VG Analitical 7070 mass spectrometer coupled to a Varian, Model 3700, gas chromatograph, as were negative (−) ion CI, and linked scan EI mass spectral data. High resolution electron ionization (HREI) and high resolution field desorption (HRDF) mass spectral data were obtained on a Finnigan MAT 731 mass spectrometer. Low and high resolution fast atom bombardment (FAB) mass spectra were obtained on a VG ZAB-HF mass spectrometer.

Physical Characterization of Eudistomins—Results

Eudistomin A (MW327): Yellow oil; UV $\lambda_{max}$ CH$_3$OH ($\epsilon$) 210 (17,600), 229 (sh), 258 (13,600), 272 (sh), 285 (sh), 326 (11,600), 373 (6400) and 389 nm (sh); IR $\nu_{max}$ CHCl$_3$ 3460, 3010, 1680 (weak), 1605 (weak), 1575 (weak), 1555 (weak) cm$^{-1}$; $^1$H NMR (360 MHz, acetone-d$_6$) 10.90 (br s, H-9), 10.33 (br s, H-1'), 8.29 (d, J=5.1 Hz, H-3), 7.91 (s, H-8), 7.82 (d, J=5.1 Hz, H-4), 7.79 (s, H-5), 7.08 (m, H-3'), 7.08 (m, H-5') and 6.34 ppm (m, H-4'); $^{13}$C NMR (acetone-d$_6$) 148.4 (s, C-6), 138.3 (d, C-3), 136.8 (s, C-9a), 136.7 (s, C-1), 132.2 (s, C-8a), 130.0 (s, C-2'), 129.2 (s, C-4b), 122.4 (s, C-4a), 120.7 (d, C-5'), 116.7 (d, C-8), 112.5 (s, C-7), 112.4 (d, C-4), 110.1 (d, C-5), 107.2 (d, C-3'), 109.0 (d, C-4'); HRFABMS Calcd for C$_{15}$H$_{11}$BrN$_3$O: 328.0085 (M+H). Found 328.0067 m/z (M+H).

Eudistomin A Acetate: Eudistomin A was treated with acetic anhydride and pyridine to give its acetate: UV $\lambda_{max}$ (CH$_3$OH ($\epsilon$) 207 (17,000), 222 (sh), 257 (12,000), 283 (sh), 303 (sh), 314 (9,800), 367 (6,600), 380 (sh); IR $\nu_{max}$ CHCl$_3$ 3460, 3020, 1760, 1630, 1600, 1575 cm$^{-1}$; $^1$H NMR (360 MHz, acetone-d$_6$) 10.92 (br s, H-9), 10.65 (br s, H-1'), 8.37 (d, J=5.1 Hz, H-3), 8.11 (s, H-5), 8.02 (s, H-8), 7.92 (d, J=5.1 Hz, H-4), 7.11 (m, H-3'), 7.10 (m, H-5'), 6.35 (m, H-4'), 2.39 (s, OCOCH$_3$); $^1$H NMR (360 MHz, CDCl$_3$) 9.82 (br s, H-9), 8.50 (br s, H-1'), 8.37 (d, J=5.3 Hz, H-3), 7.81 (s, H-5), 7.80 (s, H-8), 7.63 (d, J=5.3 Hz, H-4), 7.06 (m, H-5'), 6.81 (m, J=3.2 Hz, H-3'), 6.47 (m, J=3.2 Hz, H-4'), 2.44 (s, OCOCH$_3$); HRFABMS Calcd for C$_{17}$H$_{13}$BrN$_3$O$_2$: 370.0209 (M+H). Found: m/z 370.0189 (M+H).

Eudistomin B (MW 373): Light yellow solid; UV $\lambda_{max}$ MeOH ($\epsilon$) 368 (2294), 305 (11,750), 297 (sh), 248 (sh), 211 nm (17,904); $^1$H NMR (360 MHz, acetone-d$^6$) 3.30 (s, 3'-OCH$_3$), 3.45 (s, 6-OCH$_3$), 3.55 (m, H-3'), 6.15 (m, H-4'), 7.30 (m, H-5'), 7.78 (s, H-5), 7.82 (s, H-8), 8.00 (d, J=5.0 Hz, H-4), 8.20 (d, J=5.0 Hz, H-3). The compound shows an M+H ion by FABMS at m/z 374, with a bromine isotope peak at m/z 376.

Eudistomin C (MW 369A): [$\alpha$]$^{25}_D$−52° (c 0.4%, CH$_3$OH); UV $\lambda_{max}$ MeOH ($\epsilon$) 226 (23,400) and 287 nm (8000); IR $\nu_{max}$ CHCl$_3$ 3250 (broad), 3025, 2920, 1720 (weak), 1690 (weak), 1600 (weak) cm$^{-1}$; $^1$H NMR (360 MHz, CD$_3$CN) 3.54 (m, H-10), 2.70 m, J=14.6 Hz, H-11'), 3.25 (d, J=14.6 Hz, H-11), 4.73 (d, J=9.1 Hz, H-13), 4.87 (d, J=9.1 Hz, H-13'), 2.70 (m, H-3, H-3'), 3.01 (m, H-4), 3.54 (m, H-4'), 6.93 (s, H-5), 7.45 (s, H-8), 8.97 (br, s, H-9), 4.00 ppm (br s, H-1). HRFABMS Calcd for C$_{14}$H$_{16}$BrN$_3$O$_2$S: 370.0147 (M+H). Found 370.0173 (M+H).

Eudistomin E (MW 369B): $[\alpha]^{25}{}_D-18°$ (c 0.1, CH$_3$OH); UV $\lambda_{max}$ MeOH ($\epsilon$) 223 (18,600) and 282 nm (6700); IR $\nu_{max}$ CHCl$_3$ 3250 (broad), 3020, 2920, 1720 (weak), 1695 (weak), 1600 (weak) cm$^{-1}$; $^1$H NMR (360 MHz, CD$_3$CN) 3.52 (m, H-3, H-4' and H-10), 2.73 (m, J=14.6 Hz, H-11'), 3.25 (m, J=14.6 Hz, H-11), 4.72 (d, J=9.1 Hz, H-13), 4.86 (d, J=9.1 Hz, H-13'), 2.99 (m, H-3'), 3.25 (m, H-4), 6.73 (d, J=8.5 Hz, H-7), 7.14 (d, J=8.5 Hz, H-8), 9.08 (br s, H-9), 4.00 ppm (br s, H-1). HRFABMS Calcd for C$_{14}$H$_{16}$BrN$_3$O$_2$S: 370.0147 (M+H). Found: 370.0165 (M+H).

Eudistomins C and E were treated with acetic anhydride and pyridine to give their diacetylated derivatives whose molecular formulas and fragmentation patterns were established by HR electron ionization (EI) MS:

|  | Calculated | Found |  |
|---|---|---|---|
| C$_{18}$H$_{20}$BrN$_3$O$_4$S | 453.0358 | 453.0354 | M$^+$ |
| C$_{14}$H$_{13}$BrN$_2$O$_3$S | 367.9831 | 367.9826 | M - C$_4$H$_7$NO |
| C$_{13}$H$_{11}$BrN$_2$O$_3$ | 321.9953 | 321.9942 | 368 - CH$_2$S |
| C$_{11}$H$_9$BrN$_2$O$_2$ | 279.9847 | 279.9843 | 322 - C$_2$H$_2$O |
| C$_{11}$H$_8$BrN$_2$O | 262.9820 | 262.9812 | 280 - OH |

Eudistomin C diacetate: $[\alpha]_D{}^{25}-43°$ (c 0.8, CHCl$_3$); UV $\lambda_{max}$ MeOH ($\epsilon$) 230 (24,700) and 290 nm (5900); IR $\nu_{max}$ CHCl$_3$ 1760 and 1655 cm$^{-1}$; $^1$H NMR (360 MHz, CDCl$_3$) 5.00 (m, J=10.1 Hz, H-10), 2.79 (m, J=14.6 Hz, H-11'), 3.34 (d, J=14.6 Hz, H-11), 4.83 (d, J=9.0 Hz, H-13), 4.96 (d, J=9.0 Hz, H-13'), 2.79 (m, H-3'), 2.89 (m, H-3), 3.12 (m, H-4), 3.60 (m, H-4'), 7.16 (s, H-5), 7.56 (s, H-8), 8.76 (br s, H-9), 4.12 (br s, H-1), 7.66 (d, J=10.1 Hz, 10-NH), 1.80 (s, 10-N-COCH$_3$), 2.37 ppm (s, —OCOCH$_3$).

$^{13}$C NMR (CDCl$_3$) 69.0 (d, C-1), 32.1 (t, C-2), 71.0 (t, C-4), 54.9 (t, C-7), 20.5 (t, C-8), 109.4 (s, C-8a), 126.0 (s, C-8b), 115.6 (d, C-9), 141.2 (s, C-10), 109.5 (s, C-11), 111.8 (d, C-12), 135.6 (s, C-12a), 132.6 (s, C-13a), 46.6 (d, C-13b), 169.8 (s, C-14', OCOCH$_3$), 20.9 (q, OCOCH$_3$), 170.5 (s, NCOCH$_3$), 23.4 (q, NCOCH$_3$). HRFABMS Calcd. for C$_{18}$H$_{20}$BrN$_3$O$_4$S: 453.0358 (M+H). Found: 453.0350 (M+H).

Eudistomin E diacetate: $[\alpha]^{25}{}_D+18°$ (c 0.5, CHCl$_3$); UV $\lambda_{max}$ MeOH ($\epsilon$) 227 (14,500) and 286 nm (4400); IR, same as eudistomin C diacetate; $^1$H NMR (500 MHz, CDCl$_3$) 5.05 (m, J=1.5, 3.0, 5.8, 10.0 Hz, H-10), 2.79 (dd, J=5.8, 14.6 Hz, H-11'), 3.33 (d, J=1.5, 14.6 Hz, H-11), 4.84 (d, J=9.1 Hz, H-13), 4.96 (d, J=9.1 Hz, H-13'), 3.14 (m, J=4.0, 11.3, 12.0 Hz, H-3'), 3.38 (m, J=1.5, 2.5, 11.3 Hz, H-3'), 3.10 (m, J=2.5, 9.0, 12.0 Hz, H-4), 3.60 (m, J=1.5, 4.0, 9.0 Hz, H-4'), 6.82 (d, J=8.6 Hz, H-7), 7.14 (d, J=8.6 Hz, H-8), 9.11 (br s, H-9), 4.13 (dd, J=1.5, 1.5, 3.0 Hz, H-1), 6.65 (d, J=10.0 Hz, 10-HN), 1.81 (s, —NCOCH$_3$), 2.36 ppm (s, —OCOCH$_3$);

$^{13}$C NMR (CDCl$_3$) 69.0 (d, C-1), 32.1 (t, C-2), 71.0 (t, C-4), 55.0 (t, C-7), 22.5 (t, C-8), 108.1 (s, C-8a), 125.8 (s, C-8b), 110.5 (s, C-9), 141.5 (s, C-10), 117.0 (s, C-11), 111.3 (d, C-12), 135.6 (s, C-12a), 132.9 (s, C-13a), 46.8 (d, C-13b), 169.6 (s, OCOCH$_3$), 20.9 (q, OCOCH$_3$), 170.5 (s, NCOCH$_3$), 23.5 (q, NCOCH$_3$). HRFABMS Calcd. for C$_{18}$H$_{20}$BrN$_3$O$_4$S: 453.0358 (M+H). Found: 453.0354 (M+H).

Eudistomin F (MW 427): Light yellow solid; UV $\lambda_{max}$ CH$_3$OH ($\epsilon$) 287 (4100), 225 nm (10,800); $^1$H NMR (360 MHz, CD$_3$CN) 8.27 (br s, 9-NH), 7.43 (s, H-8), 7.03 (s, H-5), 5.85 (d, J=9.0 Hz, 10-NHCOCH$_2$OH), 4.95 (d, J=8.8 Hz, H-13), 4.80 (d, J=8.8 Hz, H-13'), 4.63 (m, J=9.0 Hz, H-10), 4.10 (br s, H-1), 3.60 (m, H-4'), 3.48 (m, 10-NHCOCH$_2$OH), 3.30 (m, J=16.0 Hz, H-11), 3.15 (m, H-4), 2.85 (m, H-3), 2.80 (m, J=16.0 Hz, H-11'), 2.78 (m, H-3'). The compound shows a molecular ion at m/z 427 in the EI mass spectrum with a bromine isotope peak at m/z 429. HREIMS established the fragment ions as C$_{12}$H$_{11}$BrN$_2$O$_2$S (m/z 325.9723; requires 325.9723) and C$_{11}$H$_9$BrN$_2$O$_2$ (m/z 279.9851; requires 279.9847). FABMS shows pseudomolecular ions at m/z 428 and 426 in the positive and negative ion spectra, respectively.

Anal. Calcd for C$_{16}$H$_{18}$BrN$_3$O$_4$S: mol. wt, 427.0200. Found: mol. wt, 427.0202 (HREIMS).

Eudistomin K (MW 353A); Slightly yellow oil; $[\alpha]^{25}{}_D-102°$ (c 0.2, CH$_3$OH); UV $\lambda_{max}$ CH$_3$OH ($\epsilon$) 229 (17,000), 284 (4000), 295 nm (sh). IR $\nu_{max}$ CHCl$_3$ 3460, 3020, 2960, 2920, 2850, 1690 (weak), 1660 (weak), 1640 (weak), 1580 (weak) cm$^{-1}$; $^1$H NMR (360 MHz, CD$_3$CN) 9.23 (br s, H-9), 7.52 (d, J=1.5 Hz, H-8), 7.36 (d, J=8.4 Hz, H-5), 7.16 (dd, J=1.5, 8.4 Hz, H-6), 4.91 (d, J=9.2 Hz, H-13'), 4.77 (d, J=9.2 Hz, H-13), 4.05 (br s, H-1), 3.55 (m, H-4' and H-10), 3.29 (m, H-11), 3.05 (m, H-4), 2.78 ppm (m, H-11', H-3 and H-3'); FABMS (positive ion spectrum, thioglycerol), m/z 354 (M$^+$+H), 356 (M+H+2)$^+$. HRFABMS Calcd. for C$_{14}$H$_{17}$BrN$_3$O$_5$: 354.0276 (M+H). Found: 354.0272 (M+H).

Eudistomin L (MW 353B): Slightly yellow oil; $[\alpha]^{25}{}_D-77°$ (c 0.2, CH$_3$OH); UV $\lambda_{max}$ MeOH ($\epsilon$) 228 (26,600), 280 (sh), 288 (6,100), 297 nm (sh); IR $\nu_{max}$ CHCl$_3$ 3460, 3020, 2960, 2920, 2850, 1690 (weak), 1590 (weak) cm$^{-1}$; $^1$H NMR (360 MHz, CD$_3$CN) 9.30 (br s, H-9), 7.60 (d, J=1.3 Hz, H-5), 7.28 (d, J=8.5 Hz, H-8), 7.20 (dd, J=1.3, 8.5 Hz, H-7), 4.90 (d, J=9.1 Hz, H-13), 4.77 (d, J=9.1 Hz, H-13'), 4.06 (br s, H-1), 3.54 (m, H-4' and H4'), 3.29 (m, H-11), 3.04 (m, H-4), 2.77 ppm (m, H-3, H-3' and H-11'); FABMS (positive ion spectrum, thioglycerol) m/z 354 (M$^+$+H), 356 (M+H+2)$^+$. HRFABMS Calcd. for C$_{14}$H$_{17}$BrN$_3$OS: 354.0276(M+H). Found: m/z 354.0282 (M+H).

Eudistomin D (MW 262A): Yellow oil; UV $\lambda_{max}$ ($\epsilon$) CH$_3$OH 201 (20,700), 213 (20,000), 232 (24,000), 246 (17,600), 286 (8300), 294 (12,200), 361 (3600), 373 nm (sh); IR $\nu_{max}$ CHCl$_3$ 3500, 3020, 1600 cm$^{-1}$; $^1$H NMR (360 MHz, acetone-d$_6$) 11.0 (brs, H-9), 8.98 (s, H-1), 8.55 (d, J=5.4 Hz, H-3), 8.39 (d, J=5.4 Hz, H-4), 7.58 (d, J=8.7 Hz, H-8), 7.36 ppm (d, J=8.7 Hz, H-7); MS m/z 262 (M$^+$), 264 (M+2)$^+$(EI); Calcd for C$_{11}$H$_8$BrN$_2$O: 262.9819 (M+H). Found: m/z 262.980 (m$^+$+H) (HRFABMS).

Eudistomin D Acetate (MW 346): Eudistomin D was treated with acetic anhydride in pyridine at room temperature overnight to give its acetate as a yellow oil; UV $\lambda_{max}$ CH$_3$OH ($\epsilon$) 204 (16,500), 231 (22,500), 255 (sh), 283 (8200), 320 (4000), 333 nm (5200); IR $\nu_{max}$ CHCl$_3$ 3040, 1780, 1710 cm$^{-1}$; $^1$H NMR (360 MHz, CD$_2$Cl$_2$), 9.58 (s, H-1), 8.71 (d, J=5.5 Hz, H-4), 8.67 (d, J=5.5 Hz, H-3), 8.40 (d, J=8.8 Hz, H-8), 7.43 (d, J=8.8 Hz, H-7), 2.95 (s, —NCOCH$_3$), 2.43 ppm (s, —OCOCH$_3$); FABMS (positive ion spectrum, thioglycerol) m/z 347 (M$^+$+H), 349 (M+H+2)$^+$. HRFABMS Calcd. for C$_{15}$H$_{12}$BrN$_2$O$_3$: 347.0031 (M+H). Found: m/z 347.0038 (M+H).

Eudistomin J (MW 262B) has not been isolated. A mixture containing eudistomin D as the major component and eudistomin J as the minor component was treated with acetic anhydride in pyridine at room temperature overnight and then was subjected to silica gel HPLC to give the eudistomin D acetate (described above) and eudistomin J acetate (MW 346) as a yellow oil: UV $\lambda_{max}$ ($\epsilon$) CH$_3$OH 205 (31,4000), 229 (42,800), 258 (sh), 266 (17,700), 280 (sh), 288 (24,500), 316 (9300), 327 nm (10,300); $^1$H NMR (360 MHz, CD$_2$Cl$_2$) 9.49 (s, H-1), 8.72 (s, H-8), 8.63 (d, J=5.3 Hz, H-3), 7.92 (d, J=5.3 Hz, H-4), 7.89 (s, H-5), 2.94 (s, —NCOCH$_3$), 2.42 ppm (s, —OCOCH$_3$); FABMS (positive ion spectrum, thioglycerol) m/z 347 (M$^+$+H), 349 (M+H+2)$^+$. HRFABMS Calcd. for C$_{15}$H$_{12}$BrN$_2$O$_3$: 347.0031 (M+H). Found: m/z 347.0029 (M+H).

Eudistomin G (MW 313B): Colorless needles; mp 204°-206° C.; UV $\lambda_{max}$ C$_6$H$_{12}$ ($\epsilon$) 203 (19,000), 219 (21,500), 238 (sh), 250 (10,000), 258 (sh), 282 (11,700), 299 (8700), 307 (8400), 346 (5100), and 362 nm (7600); IR $\nu_{max}$(KBr) 3360, 3080, 2960, 1630, 1605, 1570, 1480, 1430, 1285, 1245, 1140, 800 cm$^{-1}$; $^1$H NMR (360 MHz, CD$_2$Cl$_2$), 8.49 (d, J=5.1 Hz, H-6), 7.99 (d, J=5.1 Hz, H-7), 8.04 d, J=8.3 Hz, H-8), 7.42 (dd, J=8.3, 1.0 Hz, H-9), 7.77 (d, J=1.0 Hz, H-11), 3.28 (m, H-3), 2.08 (m, H-2), 4.26 (m, H-1), 10.93 (s, H-13); $^{13}$C NMR (CDCl$_3$), 135.8 (s, C-9a), 141.0 (s, C-1), 138.3 (d, C-3), 115.5 (d, C-4), 121.8 (s, C-4a), 128.4 (s, C-4b), 122.5 (d, C-5), 123.1 (d, C-6), 119.8 (s, C-7), 114.6 (d, C-8), 135.0 (s, C-8a), 176.3 (s, C-13), 21.4 (t, C-12), 34.5 (t, C-11), 61.8 (t, C-10); HREIMS m/z 313.0195 (M) (Calcd for C$_{15}$H$_{12}$BrN$_3$, 313.0215); FABMS m/z 314 (M+H) and 316 (M+2+H).

Eudistomin H (MW 313A): Yellow powder; mp 140°-142° C.; UV $\lambda_{max}$C$_6$H$_{12}$ ($\epsilon$) 203 (24,700), 221 (34,200), 236 (sh), 250 (12,400), 258 (10,000), 280 (sh), 286 (17,000), 295 (sh), 306 (9400), 355 (sh) and 369 nm (8400); IR $\epsilon_{max}$ KBr 3360, 3060, 2960, 2935, 1630, 1605, 1480, 1285, 1270, 1155, 800 cm$^{-1}$; 1H NMR (360 MHz, CD$_2$Cl$_2$), 8.50 (d, J=5.1 Hz, H-6), 7.99 (d, J=5.1 Hz, H-7), 8.31 (d, J=1.4 Hz, H-8), 7.66 (dd, J=8.7, 1.4 Hz, H-10), 7.52 (d, J=8.7 Hz, H-11), 3.30 (m, H-3), 2.09 (m, H-2), 4.23 (m, H-1), 11.01 (s, H-13); $^{13}$C NMR (CDCl$_3$), 136.3 (s, C-9a), 139.3 (s, C-1), 138.5 (d, C-3), 116.0 (d, C-4), 123.0 (s, C-4a), 128.4 (s, C-4b), 124.5 (d, C-6), 112.8 (s, C-6), 131.2 (d, C-7), 113.4 (d, C-8), 135.3 (s, C-8a), 176.8 (s, C-13), 21.8 (t, C-12), 34.9 (t, C-11), 62.2 (t, C-10); HREIMS, Calcd. for C$_{15}$H$_{12}$BrN$_3$: 313.0215 (M). Found: 313.0208 (M).

Eudistomin I (MW 235): Colorless powder, mp 153°-155° C.; UV $\lambda_{max}$C$_6$H$_{12}$ ($\epsilon$) 201 (sh), 217 (23,800), 235 (sh), 249 (6500), 256 (6000), 279 (10,700), 293 (4700), 302 (sh), 353 (sh), and 365 nm (7000); IR J (KBr) 3360, 3300, 3050, 2980, 2930, 1650, 1620, 1450, 1430, 1285, 1255, 1140, 750 cm$^{-1}$; $^1$H NMR (360 MHz, CD$_2$Cl$_2$), 8.48 (d, J=5.0 Hz, H-6), 8.03 (d, J=5.0 Hz, H-7), 8.18 (d, J=7.8 Hz, H-8), 7.31 (t, J=7.8, 7.1 Hz, H-9), 7.58 (t, J=8.1, 7.1 Hz, H-10), 7.62 (d, J=8.1 Hz, H-11), 3.30 (m, H-3), 2.08 (m, H-2), 4.27 (m, H-1), 10.91 (s, H-13); $^{13}$C NMR (CDCl$_3$), 135.8 (s, C-9a), 140.7 (s, C-1), 138.1 (d, C-3), 116.0 (d, C-4), 121.2 (s, C-4a), 129.4 (s, C-4b), 121.7 (d, C-5), 120.0 (d, C-9), 128.4 (d, C-7), 111.9 (d, C-8), 135.3 (s, C-8a), 176.7 (s, C-13), 21.8 (t, C-12), 34.9 (t, C-11), 62.1 (t, C-10); HREIMS, Calcd for C$_{15}$H$_{13}$N$_3$: 235.1109. Found: m/z 235.1094 (M).

Eudistomin G Amine: Eudistomin G was reduced with sodium borohydride to the amine (Scheme 2). FABMS m/z 316 (M+H) with 318 (M+2+H).

Eudistomin G Amine Acetate: Eudistomin G amine was acetylated with acetic anhydride in pyridine (Scheme 2). UV $\lambda_{max}$CH$_3$OH ($\epsilon$) 240 (21,000), 296 (13,900) and 349 nm (4600); IR $\nu_{max}$CHCl$_3$ 1650 (v. strong) and 1475 (strong) cm$^{-1}$;

$^1$H NMR (360 MHz, CD$_2$Cl$_2$), 8.27 (d, J=5.1 Hz, H-6), 7.70 (d, J=5.1 Hz, H-7), 7.82 (d, J=8.4 Hz, H-8), 7.28 (dd, J=8.4, 1.6 Hz, H-9), 7.45 (d, J=1.6 Hz, H-11), 5.85 (d, J=6.7 Hz, H-4), 2.67 (m, J=6.7 Hz, H-3), 2.12 (m, H-2), 3.64 (m, H-1), 11.23 (s, H-13), 2.14 (s, —N-COCH$_3$); FABMS m/z 358 (M+H) and 360 (M+2+H).

Eudistomin M (MW 249) has not been isolated. A mixture containing eudistomin C as the major component and eudistomin M as the minor component was treated with acetic anhydride in pyridine at room temperature overnight and then subjected to silica gel HPLC with chloroform to give eudistomin C acetate (described above) and eudistomin M acetate (MW 291) as a yellow oil: UV $\lambda_{max}$CH$_3$OH ($\epsilon$) 202 (11,900), 223 (10,400), 251 (7900), 277 (sh), 288 (sh), 311 (5400), 363 (4700), 378 nm (4500); IR $\nu_{max}$CHCl$_3$ 3500, 3030, 1760, 1570 cm$^{-1}$; $^1$HNMR (360 MHz; acetone-d-6) 10.40 (br. s, H-9), 8.77 (br s, H-1'), 8.35 (d, J=5.4 Hz, H-3), 7.86 (d, J=1.4 Hz, H-5), 7.81 (d, J=5.4 Hz, H-4), 7.63 (d, J=8.8 Hz, H-8), 7.32 (dd, J=1.4, 8.8 Hz, H-7), 7.11 (m, H-5'), 6.94 (m, J=2.4 Hz, H-3'), 6.49 ppm (m, J=2.4 Hz, H-4'): FABMS (positive ion spectrum, thioglycerol) m/z 292 (M+H)$^+$; HRFABMS, Calcd. for C$_{17}$H$_{14}$N$_3$O$_2$: 292.1095 (M+H). Found: m/z 292.1086 (M+H).

Eudistomin N (MW 246) and eudistomin O (MW 246) were isolated as a 1:1 mixture. Yellow oil: UV $\lambda_{max}$-CH$_3$OH ($\epsilon$) 198 (11,800), 216 (sh), 235 (23,900), 250 (sh), 284 (sh), 292 (10,100), 335 (2400), 347 nm (2600); IR $\nu_{max}$CHCl$_3$ 3500, 3040, 1680 (weak), 1620 (weak), 1560 cm$^{-1}$ (weak), $^1$HNMR (360 MHz, CD$_2$Cl$_2$), 10.87 (br s, H-9), 8.94 (s, H-1), 8.43 (d, J=1.7 Hz, H-5), 8.40 (d, J=5.2 Hz, H-3), 8.11 (d, J=5.2 Hz, H-4), 7.66 (dd, J=1.7, 8.7 Hz, H-7), 7.61 ppm (d, J=8.7 Hz, H-8) as eudistomin N and 10.87 (br s, H-9), 8.94 (s, H-1), 8.40 (d, J=5.0 Hz, H-3), 8.18 (d, J=8.4 Hz, H-5), 8.07 (d, J=5.0 Hz, H-4) 7.84 (d, J=1.2 Hz, H-8), 7.40 ppm (dd, J=1.2, 8.4 Hz, H-6) as eudistomin O; FABMS (positive ion spectrum, thioglycerol) m/z 247 (M+H)$^+$, 249 (M+2+H)$^+$; HRFABMS, Calcd. for C$_{11}$H$_8$BrN$_2$: 246.9868 (M+H). Found: m/z 246.9871 (M+H).

Eudistomin P (MW 329): Yellow powder, mp 128°-130° C.; UV $\lambda_{max}$MeOH ($\epsilon$) 201 (sh) 216 (28,100); 249 (11,800), 300 (13,400), 318 (sh) 372 (4600), 381 nm (4800); IR $\nu_{max}$CHCl$_3$ 3600, 3450, 3020, 2910, 1570, 1530 cm$^{-1}$; $^1$HNMR (360 MHz acetone-d-6) 11.08 (s, H-13), 8.42 (d, J=5.4, H-3), 8.10 (s, H-8), 8.09 (d, J-5.4 Hz, H-4), 7.84 (s, H-5), 4.22 (m, H-10), 3.25 (m, H-12), 2.08 ppm (m, H-11) (360 MHz, MeOH-d-4) 8.30 (d, J=5.0, H-3), 8.02 (d, J=5.0, H-4), 7.85 (s, H-8), 7.63 (s, H-5), 4.27 (m, H-10), 3.24 (m, H-12), 2.04 ppm (m, H-11) FABMS m/z 330 (M$^+$+H), 332 (M$^+$+2+H); HRFABMS (+) Calcd for C$_{15}$H$_{13}$BrN$_3$O: 330.0258 (M+H). Found: m/z 330.0242 (M+H) ($\Delta$1.6 mmu).

Eudistomin Q (MW 251): Yellow powder, mp 120°-125° C.; UV $\lambda_{max}$ CH$_3$OH ($\epsilon$) 198 (17,900), 214 (19,900), 231 (sh), 240 (sh), 250 (sh), 280 (sh), 288 (8000), 317 (sh), 348 (2500), 362 (2500), 382 nm (sh);

IR $\nu_{max}$ CHCl$_3$ 3500, 3020, 2930, 1580 cm$^{-1}$; $^1$H NMR (d, J=5.0 Hz, H-4), 7.71 (d, J=8.8 Hz, H-8), 7.67 (d, J=1.0 Hz, H-5), 7.20 (dd, J=8.8, 1.0 Hz, H-7), 4.24 (m, H-10), 3.25 (m, H-12), 2.10 ppm (m, H-11); HRFABMS, Calcd. for C$_{15}$H$_{14}$N$_3$O: 252.1134 (M+H); Found: m/z 252.1137 (M+H).

Biological Characterization of Eudistomins—Materials and Methods Primary Antiviral Screening:

Extracts and column fractions were monitored for antiviral activity by a primary screening procedure (A.

C. Schroeder, R. G. Hughes, Jr., A. Block; J. Med. Chem., 1981, 24, 1078) developed by Dr. Robert G. Hughes, Jr., Roswell Park Memorial Institute, Buffalo, NY 14263.

Stock cultures of monkey kidney cells (CV-1 line) were obtained from Dr. Hughes and maintained in 75 sq. cm. Corning culture flasks with 30 ml of culture medium at 36° C. (10% $CO_2$ atmosphere).

The culture medium was made up of 1 L Gibco minimum essential media and non-essential amino acids (containing Earle's salts), 50 ml of Gibco calf serum and 10 ml of Gibco Pen-Strep mixture (MEM). Cultures were prepared by aspirating the cells and washing twice with 10 ml of a sterile filtered phosphate buffer solution (PBSA) made up of sodium chloride (8 g/L), potassium chloride (0.2 g/L), sodium phosphate, dibasic (1.5 g/L) and potassium phosphate, monobasic (0.25 g/L) in water. The cells were then dislodged by incubating them with 2 ml of a trypsin/EDTA solution containing trypsin I-250 (200 mg), EDTA (20 mg), and PBSA (100 ml). The trypsin/EDTA solution was sterile-filtered. Once the cells were dislodged they were diluted to 30 ml with culture medium. The cells were then counted with a hemocytometer and $3 \times 10^6$ cells were added to each new culture dish with 30 ml (total) of culture media. The cells were transferred weekly.

To prepare assay plates, $1 \times 10^6$ cells were deposited in each well of a Costar Cluster 6 assay dish with 2 ml (total) of culture media and allowed to incubate for 24 hours. The wells were then aspirated and 0.5 ml of culture media containing 200 plaque forming units (pfu) of herpes simplex virus type I (HSV-I), obtained from Dr. Hughes, was added. The cultures were then incubated for 1 to 2 hours to allow for infection. A solution of methyl cellulose (MC-4000, 2 ml) was layered over the cells after infection to stop the spread of the virus. The MC-4000 solution was made up of a 1 L packet of Gibco minimum essential media+non-essential amino acids (with Earle's salts) dissolved in 500 ml of water ($2 \times MEM$) with 50 ml of calf serum and 10 ml of Pen-Strep solution, 500 ml of a 2% w/v suspension of methyl cellulose (autoclaved, MC-4000).

The sample to be assayed was then deposited on a 12.5-mm sterile paper assay disk and the disk was placed in the assay well. The cultures were incubated for 48 hours, then stained with neutral red media prepared by adding 500 ml of $2 \times MEM$ to 500 ml of 4% w/v methyl cellulose (autoclaved, MC-15), and 30 ml of Gibco neutral red solution (3.333 mg/ml). After 24 hours of incubation, the plates were read. The zone of cytotoxicity appeared as a non-stained area and was reported as the diameter in mm, 36 mm being the maximum (diameter of well). Antiviral activity as indicated by inhibition of viral plaque formation was qualitatively assigned; complete inhibition (+++), a few plaques around the outside of the well (++), definite inhibition (+), questionable inhibition (±), and no inhibition (−).

Primary Antimicrobial Screening

Antibacterial and antifungal activities were determined by the methods described in the following published reference: (Shaw, P. D.; McClure, W. O.; Van Blaricom, G.; Sims, J.; Fenical, W.; Rude, J. in "Food-Drugs from the Sea Proceedings 1974", Webber, H. H.; Ruggieri, G. D., eds.; Marine Technol. Soc.: Washington, D.C., 1976; pp. 429–33).

Secondary Antiviral Screening

These tests were performed by the methods described in the following published reference: (H. E. Renis, C. A. Hollowell, and G. E. Underwood, J. Med. Chem., Vol. 10, pp. 777–782, (1967)). Both DNA and RNA containing viruses were used.

Biological Characterization of Eudistomins—Results

Antimicrobial and antiviral activity are shown on Chart I.

The administration of eudistomins is useful prophylactically and therapeutically for preventing and treating viral infections. For example, pharmaceutical compositions containing the active ingredients are useful in prophylactic or therapeutic treatment of humans and animals infected or likely to be infected with viruses, e.g., hepatitis, virus, rubella, rubeola, influenza, encephalitis viruses (i.e., arboviruses such as western or eastern equine encephalitis virus, Semliki Forest virus), herpes viruses (types 1 or 2 herpes simplex virus, cytomegalovirus, varicella-zoster and infectious bovine rhinotracheitis virus), rabies, enteroviruses (picornaviruses, echoviruses, coxsackie viruses), parainfluenza viruses, respiratory syncytial virus, sendai virus, poliomyelitis viruses, yellow fever, Epstein-Barr virus (infectious mononucleosis), small pox, Dengue virus, common cold virus (rhinoviruses, coronaviruses, etc.), adenoviruses, polyomaviruses, papovaviruses, RNA-tumor viruses (e.g., feline leukemia virus, avian leukosis virus, avian sarcoma viruses), B virus, aleutians disease of mink, arena viruses, blue tongue virus of sheep, bovine viral diarrhea-mucosal disease virus, canine distemper virus, canine hepatitis virus, canine herpesvirus, equine abortion virus, infectious equine anemia virus, fowl pox virus, hog cholera virus, Marek's disease, mink enteritis virus, Newcastle disease virus, porcine enterovirus, pseudorabies virus, foot and mouth disease virus, reoviruses, and all other viruses or diseases of viral origin (for example, slowly progressing diseases that may be of viral origin such as multiple-sclerosis or Acquired Immune Deficiency Syndrome) that are sensitive to the antiviral actions of the eudistomins.

The dosage administered will be dependent upon the identity of the viral infection, the type of host involved, its age, health, weight, kind of concurrent treatment, if any, frequency of treatment and therapeutic ratio.

Illustratively, dosage levels of the administered active ingredients can be: intravenous, 0.1 to about 20 mg/kg; intraperitoneal, 0.1 to about 100 mg/kg; subcutaneous, 0.1 to about 100 mg/kg; intramuscular, 0.1 to about 100 mg/kg; orally, 0.1 to about 200 mg/kg, and preferably about 1 to 100 mg/kg; intranasal instillation, 0.1 to about 20 mg/kg; and aerosol, 0.1 to about 20 mg/kg of animal (body) weight.

Expressed in terms of concentration, an active ingredient can be present in the compositions of the present invention for localized use about the cutis, intranasally, pharyngolaryngeally, bronchially, broncholially, intravaginally, rectally, or ocularly in a concentration of from about 0.1 to about 50% w/w of the composition; preferably about 1 to about 20% w/w of the composition; and for parenteral use in a concentration of from about 0.5 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as a talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously the tablet can be provided with a protective coating consisting of a sealing coat or enteric coat of shellac, a coating of sugar and methylcellulose and polish coating of carnauba wax.

Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, fluid unit dosage forms are prepared utilizing an active ingredient and a suitable pharmaceutical vehicle, water being preferred, or a dry powder for insufflation is used.

The active ingredients can also be admixed in animal feed. The active ingredients can conveniently be prepared in the form of a food premix. The food premix can comprise an active ingredient in admixture with an edible pharmaceutical diluent such as starch, oatmeal, flour, calcium carbonate, talc, dried fish meal and the like nontoxic, orally acceptable pharmaceutical diluents. The prepared premix is then conveniently added to the regular feed.

For use as aerosols the active ingredients can be packaged in a pressurized aerosol container together with a gaseous or liquefied propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as anti-viral agents can be easily prepared in unit dosage form with the employment of pharmaceutical materials which themselves are available in the art and can be prepared by established procedures. The following preparations are illustrative of the preparation of the unit dosage forms of the present invention, but are not intended to be limiting.

EXAMPLE 1

Hard-Gelatin Capsules

One thousand two-piece hard gelatin capsules for oral use, each capsule containing 100 mg of a eudistomin, are prepared from the following types and amounts of ingredients:

| | |
|---|---|
| a eudistomin, micronized | 100 gm |
| Lactose | 100 gm |
| Corn Starch | 20 gm |
| Talc | 20 gm |
| Magnesium stearate | 2 gm |

The eudistomin finely divided by means of an air micronizer, is added to the other finely powdered ingredients, mixed thoroughly and then encapsulated in the usual manner.

The foregoing capsules are useful for preventing or treating viral infection by the oral administration of one or two capsules one to four times a day.

Using the procedure above, capsules are similarly prepared containing eudistomin in 50, 250 and 500 mg amounts by substituting 50 gm, 250 gm and 500 gm of eudistomin for the 100 gm used above.

EXAMPLE 2

Soft Gelatin Capsules

One-piece soft gelatin capsules for oral use, each containing 250 mg of a eudistomin (finely divided by means of an air micronizer), are prepared by first suspending the compound in 0.5 ml of corn oil to render the material capsulatable and then capsulating in the above manner.

The foregoing capsules are useful for preventing or treating viral infection by the oral administration of one or two capsules one to four times a day.

EXAMPLE 3

Tablets

One thousand tablets, each containing 500 mg of a eudistomin are prepared from the following types and amounts of ingredients:

| | |
|---|---|
| A eudistomin, micronized | 500 gm |
| Lactose | 75 gm |
| Corn starch | 50 gm |
| Magnesium stearate | 4 gm |
| Light liquid petrolatum | 5 gm |

The eudistomin finely divided by means of an air micronizer, is added to the other ingredients and then thoroughly mixed and slugged. The slugs are broken down by forcing through a Number Sixteen screen. The resulting granules are then compressed into tablets, each tablet containing 500 mg of the eudistomin.

The foregoing tablets are useful for preventing or treating viral infection by the oral administration of one or two tablets one to four times a day.

Using the procedure above, tablets are similarly prepared containing a eudistomin in 250 mg and 100 mg amounts by substituting 250 gm and 10 gm of a eudistomin for the 500 gm used above.

EXAMPLE 4

Oral Suspension

One thousand ml of an aqueous suspension for oral use, containing in each teaspoonful (5 ml) dose, 500 mg of a eudistomin, is prepared from the following types and amounts of ingredients:

| | |
|---|---|
| A eudistomin, micronized | 100 gm |

-continued

| | |
|---|---|
| Citric acid | 2 gm |
| Benzoic acid | 1 gm |
| Sucrose | 700 gm |
| Tragacanth | 5 gm |
| Lemon Oil | 2 gm |
| Deionized water, q.s. | 1000 ml. |

The citric acid, benzoic acid, sucrose, tragacanth and lemon oil are dispersed in sufficient water to make 850 ml of suspension. The eudistomin, finely divided by means of an air micronizer, is stirred into the syrup until uniformly distributed. Sufficient water is added to make 1000 ml.

The composition so prepared is useful for preventing or treating viral infection at a dose of 1 tablespoonful (15 ml) three times a day.

EXAMPLE 5

A sterile aqueous suspension for parenteral injection, containing in 1 ml 300 mg of a eudistomin, is prepared from the following types and amounts of ingredients:

| | |
|---|---|
| A eudistomin, micronized | 300 gm |
| Polysorbate 80 | 5 gm |
| Methylparaben | 2.5 gm |
| Propylparaben | 0.17 gm |
| Water for injection, q.s. | 1000 ml. |

All the ingredients, except the eudistomin, are dissolved in the water and the solution sterilized by filtration. To the sterile solution is added the sterilized eudistomin, finely divided by means of an air micronizer, and the final suspension is filled into sterile vials and the vials sealed.

The composition so prepared is useful for preventing or treating viral infection at a dose of 1 milliliter (1M) three times a day.

EXAMPLE 6

Suppository, Rectal and Vaginal

One thousand suppositories, each weighing 2.5 gm and containing 150 mg of a eudistomin are prepared from the following types and amounts of ingredients:

| | |
|---|---|
| A eudistomin, micronized | 150 gm |
| Propylene glycol | 150 gm |
| Polyethylene glycol, 4000 q.s. | 2,500 gm |

The eudistomin is finely divided by means of an air micronizer and added to the propylene glycol and the mixture passed through a colloid mill until uniformly dispersed. The polyethylene glycol 40000 is melted and the propylene glycol dispersion added slowly with stirring. The suspension is poured into unchilled molds at 40° C. The composition is allowed to cool and solidify and then removed from the mold and each suppository foil wrapped.

The foregoing suppositories are inserted rectally or vaginally for preventing or treating viral infection.

EXAMPLE 7

Intranasal Suspension

One thousand ml of a sterile aqueous suspension for intranasal instillation, containing in each ml 150 mg of a eudistomin, is prepared from the following types and amounts of ingredients:

| A eudistomin, micronized | 150 gm |
|---|---|
| Polysorbate 80 | 5 gm |
| Methylparaben | 2.5 gm |
| Propylparaben | 0.17 gm |
| Deionized water, q.s. | 1000 ml. |

All the ingredients, except the eudistomin, are dissolved in the water and the solution sterilized by filtration. To the sterile solution is added the sterilized eudistomin, finely divided by means of an air micronizer, and the final suspension is aseptically filled into sterile containers.

The composition so prepared is useful for preventing or treating viral infection by intranasal instillation of 0.2 to 0.5 ml given one to four times per day.

EXAMPLE 8

Animal Feed

One thousand grams of feed premix is prepared from the following types and amounts of ingredients:

| A eudistomin | 20 gm |
|---|---|
| Soybean meal | 400 gm |
| Fish meal | 400 gm |
| Wheat germ oil | 50 gm |
| Sorghum molasses | 130 gm |

The ingredients are mixed together and pressed into pellets.

The premix can be fed directly to laboratory animals, i.e., rats and mice, for preventing or treating viral infection.

For larger animals the premix can be added to the animal's regular feed in an amount calculated to give the desired dose of eudistomin. For example, one part of premix is added to 2.5 parts of a cat's regular feed to provide the desired dose of 200 mg/kg/day for a cat of 2.5 kg.

An active ingredient can also be present, as shown in Examples 12–15 in the undiluted pure form for use locally about the cutis, intranasally, pharyngolaryngeally, bronchially, broncholially or orally in an amount calculated to give the desired dose of eudistomin. For example, one part of premix is added to 2.5 parts of a cat's regular feed to provide the desired dose of 200 mg/kg/day for a cat of 2.5 kg.

An active ingredient can also be present, as shown in Examples 12–15 in the undiluted pure form for use locally about the cutis, intranasally, pharyngolaryngeally, bronchially, broncholially or orally.

EXAMPLE 9

Powder

Five hundred grams of a eudistomin in bulk form is finely divided by means of an air micronizer. The micronized powder is placed in a shaker-type container.

The foregoing composition is useful for preventing or treating viral infection at localized sites by applying the powder one to four times per day.

EXAMPLE 10

Oral Powder

One thousand grams of a eudistomin in bulk form is finely divided by means of an air micronizer. The micronized powder is divided into individual doses of 250 mg and packaged.

The foregoing powders are useful for preventing or treating viral infection by the oral administration of one or two powders suspended in a glass of water, one to four times per day.

EXAMPLE 11

Insufflation

One thousand grams of a eudistomin in bulk form is finely divided by means of an air micronizer.

The foregoing composition is useful for preventing or treating viral infection by the inhalation of 30 to 75 mg one to four times per day.

EXAMPLE 12

Hard Gelatin Capsules

One thousand two-piece hard gelatin capsules for oral use, each capsule containing 100 mg of a eudistomin.

The eudistomin is finely divided by means of an air micronizer and encapsulated in the usual manner.

The foregoing capsules are useful for preventing or treating viral infection by the oral administration of one or two capsules one to four times a day.

Using the procedure above, capsules are similarly prepared containing eudistomin in 50, 250 and 500 mg amounts by substituting 50 gm, 250 gm and 500 gm of a eudistomin for the 100 gm used above.

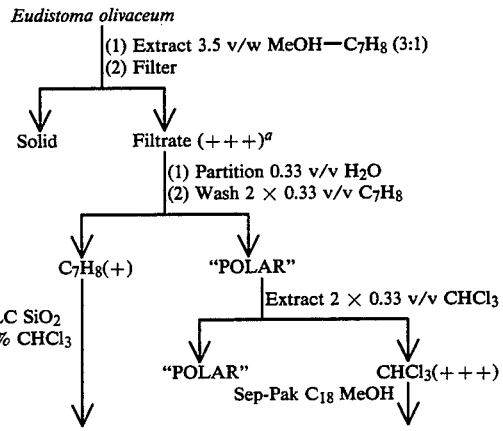

Scheme 1

Scheme 1 -continued

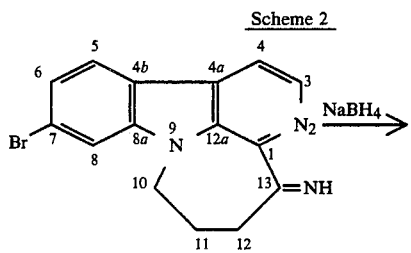

```
CRYST. FROM
HEXANE/
EtOAc
    │
    ├──────────┐         MPLC C18 MeOH/H2O
    ▼          ▼                  │
  Solid     Solution              ▼
  Recryst.  MPLC C18       MPLC SiO2 MeOH/CHCl3
  from      MeOH/H2O              │
  Dichloro-                       ▼
  methane              HPLC SiO2 MeOH/CHCl3
    │          │                  │
    ▼          ▼                  ▼
Eudistomin G  Eudistomins H and I Eudistomins C, E, D, J^b,
                        A, K, L, F,
                        B, M^b, N^c,
                        O^c, P, Q
```

[a] Pluses indicate level of antiviral activity at 3 μg per disk.
[b] Isolated as acetyl derivatives.
[c] Isolated as a mixture of Eudistomins N and O.

Scheme 2

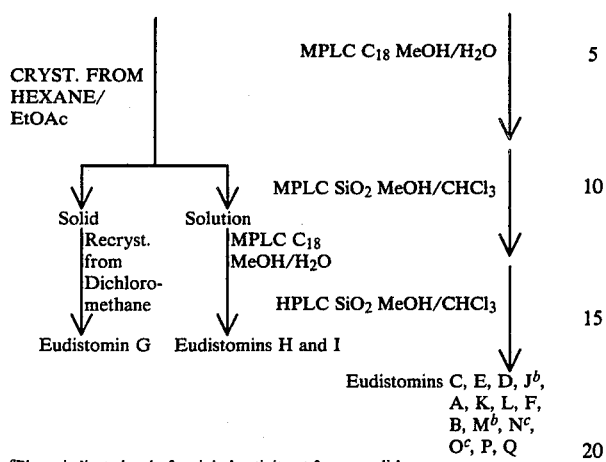

Eudistomin G

Scheme 2 -continued

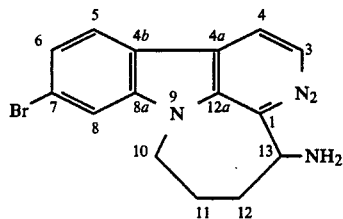

Eudistomin G amine

↓ Ac2O/Pyridine

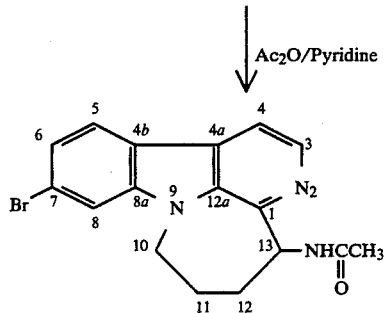

Eudistomin G amine acetate

CHART I

| | | Biological Characterization of Eudistomins | | | | | | | | | |
|---|---|---|---|---|---|---|---|---|---|---|---|
| | Primary | Primary Antimicrobial Screen[1] | | | | Secondary Antiviral Screen[2] | | | | | |
| Eudi-stomin | Antiviral Screen HSV-1 | Bacillus subtillis | Escherichia coli | Saccharo-myces cerevisiae | Penicillium atrovenetum | PR-8 | COE | HA-1 | ER | HSV-I | HSV-II | VACC |
| A | − at 500 ng/well | 0 | 0 | 0 | 0 | | | | | | | |
| A acetate | + at 1000 ng/well | 0 | 0 | 0 | 0 | | | | | | | |
| B | − at 500 ng/well | | | not tested | | | | | | | | |
| C ++ at 25 ng | + at 10 ng/well | 26 (clear) | 22 (clear) | 27 (clear) | | 4/0 4/0 | 2/4 2/4 | 0/4 4/0 | 2/4 2/4 | 0/4 2/4 | 0/4 2/4 | 0/4 3/4 |
| C acetate | + at 1000 ng/well | 0 | 0 | 0 | 0 | | | | | | | |
| D | + at 500 ng/well | 16 (clear) | 0 | 0 | 0 | | | | | | | |
| D acetate | + at 500 ng/well | 0 | 0 | 0 | 0 | | | | | | | |
| E +++ at 25 ng | + at 100 ng/well | 17 (clear)[3] | 0 | 0 | 0 | 4/0 | 1/4 | 4/0 | 1/4 | 1/4 | 1/4 | 2/4 |
| F | not tested | | | not tested | | | | | | | | |
| G | ± at 1000 ng/well | 0 | 0 | 0 | 0 | 1/0 | 1/0 | 1/0 | 1/1 | 1/1 | 0/1 | 0/1 |
| H | + at 500 ng/well | 0 | 0 | 20 (faint) | 0 | 1/0 | 0/0 | 0/0 | 0/0 | 0/0 | 0/0 | 0/0 |
| I | ± at 1000 ng/well | 14 (clear) | 0 | 0 | 0 | 1/0 | 1/0 | 1/0 | 1/1 | 0/2 | 0/2 | 0/1 |
| J acetate | ± at 500 ng/well | 0 | 0 | 0 | 0 | | | | | | | |
| K | + at 250 ng/well | 23 (clear) | 15 (clear) | 24 (clear) | 27 (clear) | | | | | | | |
| L | + at 100 ng/well | 27 (clear) | 20 (clear) | 28 (clear) | 32 (clear) | | | | | | | |
| M acetate | ± at 500 ng/well | 0 | 0 | 0 | 0 | | | | | | | |
| N | | | | | | | | | | | | |

CHART I-continued

Biological Characterization of Eudistomins

| Eudi-stomin | Primary Antiviral Screen HSV-1 | Primary Antimicrobial Screen[1] | | | | Secondary Antiviral Screen[2] | | | | | | |
|---|---|---|---|---|---|---|---|---|---|---|---|---|
| | | *Bacillus subtillis* | *Escherichia coli* | *Saccharomyces cerevisiae* | *Penicillium atrovenetum* | PR-8 | COE | HA-1 | ER | HSV-I | HSV-II | VACC |
| O | + at 500 ng/well | 19 (clear) | 18 (clear) | 25 (faint) | 20 (clear) | | | | | | | |
| P | ± at 1000 ng/well | 15 (clear) | 0 | 20 (faint) | 0 | | | | | | | |
| Q | − at 1000 ng/well | 14 (clear) | 0 | 0 | 0 | | | | | | | |

[1]Results are given as diameter of clear zone surrounding a 12.5 mm paper disk containing 100 μl of sample (1 mg/ml).
[2]Results are given as: zone of toxicity (cell death)/zone of viral plaque inhibition for 50 μg of compound.
[3]At 1 μg
PR-8 = Infectious bronchitis virus (RNA)
COE = Coxsackie A-21 virus (RNA)
HA-1 = Parainfluenza 3 virus (RNA)
ER = Equine rhinovirus (RNA)
HSV-I = Herpes simplex virus type 1 (DNA)
HSV-II = Herpes simplex virus type 2 (DNA)
VACC = Vaccinia virus (DNA)

CHART II

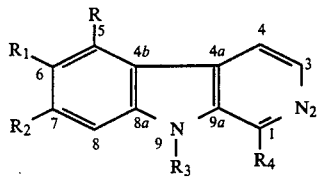

| | R | $R_1$ | $R_2$ | $R_3$ | $R_4$ |
|---|---|---|---|---|---|
| Eudistomin A | H | OH | Br | H | + |
| Eudistomin A acetate | H | COCH$_3$ | Br | H | + |

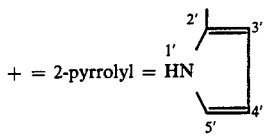

+ = 2-pyrrolyl =

Eudistomin B

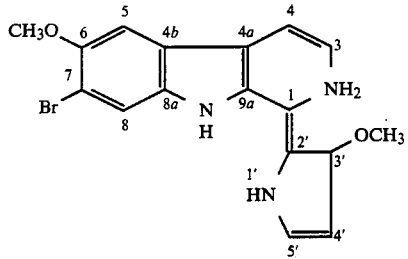

| | R | $R_1$ | $R_2$ | $R_{31}$ |
|---|---|---|---|---|
| Eudistomin C | H | OH | Br | H |
| Eudistomin E | Br | OH | H | H |
| Eudistomin C diacetate | H | COCH$_3$ | Br | —COCH$_3$ |
| Eudistomin E diacetate | Br | COCH$_3$ | H | —COCH$_3$ |

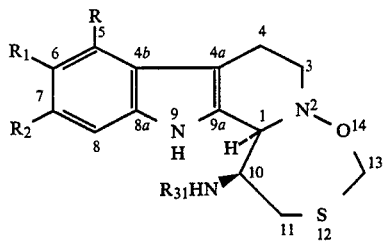

Eudistomin F

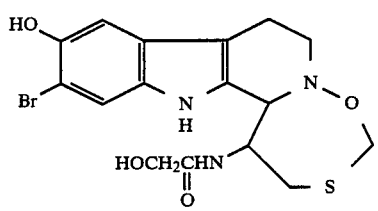

CHART II
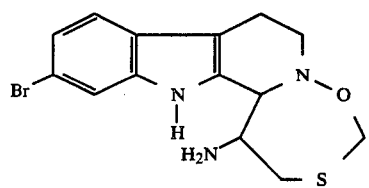
Eudistomin K
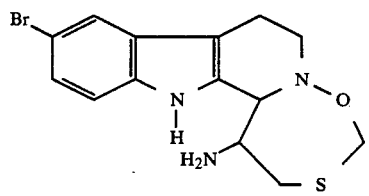
Eudistomin L
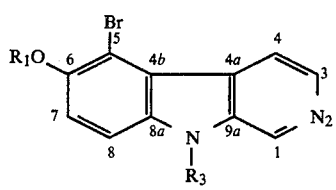
Eudistomin D   R = H
Eudistomin D   $R_1 = R_3 = -COCH_3$
acetate
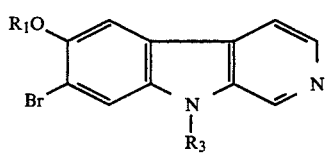
Eudistomin J   R = H
Eudistomin J   $R_1 = R_3 = -COCH_3$
acetate
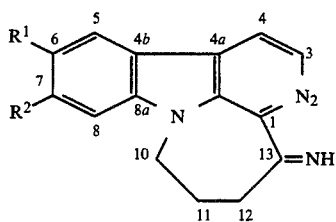
Eudistomin G   $R^1 = H, R^2 = Br$
Eudistomin H   $R^1 = Br, R^2 = H$
Eudistomin I   $R^1 = R^2 = H$
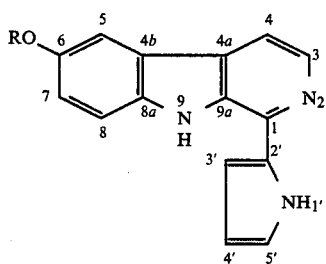
Eudistomin M   R = H
Eudistomin M   $R = -COCH_3$
acetate
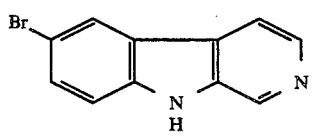
Eudistomin N
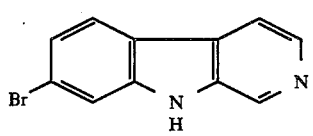
Eudistomin O

CHART II

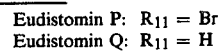
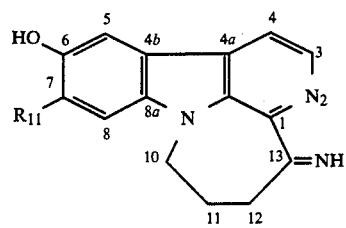

Eudistomin P: $R_{11} = Br$
Eudistomin Q: $R_{11} = H$

I claim:
1. A compound selected from the group consisting of eudistomins C, E, K, L, F, and the acylates of C and E having the formula II:

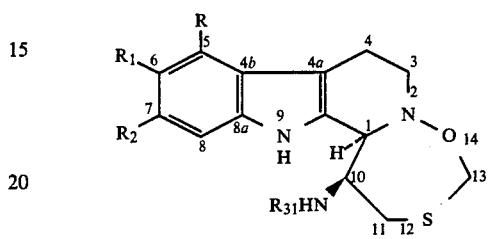

wherein the variables for each eudistomin are defined as follows:

| Eudistomin | R  | $R_1$     | $R_2$ | $R_{31}$    |
|------------|----|-----------|-------|-------------|
| C          | H  | OH        | Br    | H           |
| E          | Br | OH        | H     | H           |
| K          | H  | H         | Br    | H           |
| L          | H  | Br        | H     | H           |
| F          | H  | OH        | Br    | —COCH$_2$OH |
| C (diacetyl) | H | —OCOCH$_3$ | Br   | —COCH$_3$   |
| E (diacetyl) | Br | —OCOCH$_3$ | H   | —COCH$_3$   | or other carboxylic acylates or pharmaceutically acceptable salts.

* * * * *

UNITED STATES PATENT AND TRADEMARK OFFICE
CERTIFICATE OF CORRECTION

PATENT NO. : 4,631,149

DATED : December 23, 1986

INVENTOR(S) : Rinehart, Jr. et al.

It is certified that error appears in the above-indentified patent and that said Letters Patent is hereby corrected as shown below:

On page, 1, column 1, line 7, please insert the following:

"This invention was made with Government support under Grant No. AI04769 and GM 27029 awarded by the National Institutes of Health. The Government has certain rights in the invention."

Signed and Sealed this

Eleventh Day of April, 1995

Attest:

BRUCE LEHMAN

Attesting Officer     Commissioner of Patents and Trademarks